United States Patent
Jiang et al.

(10) Patent No.: US 11,490,602 B2
(45) Date of Patent: Nov. 8, 2022

(54) BREEDING METHOD FOR IMPROVING REPRODUCTIVE PERFORMANCE OF CHICKEN SPECIALIZED DAM LINE

(71) Applicant: Sichuan Animal Science Academy, Chengdu (CN)

(72) Inventors: Xiaosong Jiang, Chengdu (CN); Chaowu Yang, Chengdu (CN); Mohan Qiu, Chengdu (CN); Zengrong Zhang, Chengdu (CN); Chunlin Yu, Chengdu (CN); Huarui Du, Chengdu (CN); Qingyun Li, Chengdu (CN); Bo Xia, Chengdu (CN); Xiaoyan Song, Chengdu (CN); Chenming Hu, Chengdu (CN); Xia Xiong, Chengdu (CN); Li Yang, Chengdu (CN); Han Peng, Chengdu (CN); Jialei Chen, Chengdu (CN)

(73) Assignee: Sichuan Animal Science Academy, Chengdu (CN)

( * ) Notice: Subject to any disclaimer, the term of this patent is extended or adjusted under 35 U.S.C. 154(b) by 435 days.

(21) Appl. No.: 16/801,192

(22) Filed: Feb. 26, 2020

(65) Prior Publication Data
US 2020/0396971 A1  Dec. 24, 2020

(51) Int. Cl.
*A01K 67/02* (2006.01)

(52) U.S. Cl.
CPC .......... *A01K 67/02* (2013.01); *A01K 2227/30* (2013.01)

(58) Field of Classification Search
CPC .. A01K 2227/30; A01K 31/002; A01K 31/18; A01K 31/22; A01K 45/00; A01K 67/0275
USPC .................................................. 119/300, 6.8
See application file for complete search history.

(56) References Cited

U.S. PATENT DOCUMENTS

| | | | |
|---|---|---|---|
| 2005/0153317 A1* | 7/2005 | DeNise ............... | C12Q 1/6827 435/6.12 |
| 2010/0162423 A1* | 6/2010 | DeNise ............... | C12Q 1/6827 435/6.1 |
| 2016/0000046 A1* | 1/2016 | Li ......................... | A01K 31/18 362/1 |
| 2022/0136003 A1* | 5/2022 | Cinnamon ............. | C12N 9/22 800/19 |
| 2022/0183615 A1* | 6/2022 | Daines .................. | A61B 5/411 |

* cited by examiner

*Primary Examiner* — Yvonne R Abbott-Lewis
(74) *Attorney, Agent, or Firm* — Bayramoglu Law Offices LLC

(57) ABSTRACT

A breeding method for improving reproductive performance of a chicken specialized dam line includes the steps of forming an F1 generation group, forming a breeding group, screening a breeding group, forming an F2 generation group, and continuously breeding to an Fn generation group. The method includes raising in small-scale groups and natural mating for systematic selection and breeding, which effectively reduces the generation interval and has the features of easy operation and fast genetic progress, not only ensuring animal welfare, but also effectively improving production performance.

8 Claims, No Drawings

BREEDING METHOD FOR IMPROVING REPRODUCTIVE PERFORMANCE OF CHICKEN SPECIALIZED DAM LINE

CROSS REFERENCE TO THE RELATED APPLICATIONS

This application is based upon and claims priority to Chinese Patent Application No. 201910549344.0, filed on Jun. 24, 2019, the entire contents of which are incorporated herein by reference.

TECHNICAL FIELD

The present disclosure relates to breeding methods for breeding chickens, and more specifically to a breeding method for improving reproductive performance of a chicken specialized dam line.

BACKGROUND

The scientific breeding of chickens requires full consideration of the production costs and production benefits of commercial chicks when developing breeding schemes. When breeding specialized dam lines, the reproductive performance should be improved as much as possible. At present, pedigree breeding is the main breeding method for chicken reproductive performance. The pedigree breeding method requires single-cage feeding and single-cage determination. Numerous disadvantages that make the method cumbersome result, including complicated breed selection work, the inability to guarantee animal welfare and an overall slow genetic determination and management progress. Frequently, breeders, therefore, reject the pedigree breeding method in the breed selection practice of chicken specialized dam lines in China. Due to the lack of alternative breeding methods for a chicken specialized dam line, the breeding ability for the reproductive performance of chickens in China is far lower than that in developed countries in Europe as well as the United States. This severely restricts the development of the industry and food supply. Therefore, there is a need for a new breeding method for the reproductive performance of a chicken specialized dam line.

SUMMARY

One of the objectives of the present disclosure is to provide a new breeding method for improving reproductive performance of chicken specialized dam lines in response to the above drawbacks. The new method solves the technical problems that make breeding operations cumbersome, including complicated breed selection processes and the inability to guarantee animal welfare due to the single-cage feeding and single-cage determination of the pedigree breeding method in the prior art.

To solve the above technical problems, the present inventive method uses the following technical solutions.

The new aspects of the invention provide a breeding method for improving reproductive performance of a chicken specialized dam line. The breeding method includes the following steps:

step A, forming a F1 generation group, including: introducing breeding chickens of the specialized dam line as a breeding material, grouping cocks and hens in the breeding chickens and raising in brooding/breeding cages to 10 weeks of age to form a material group; then, selecting more than 2,000 cocks from the material group, raising them in small-scale groups in a plurality of cock cages to 18 weeks of age, eliminating weak cock individuals in the raising, and maintaining the number of the cocks in the cock cages after the weak cock individuals are eliminated; meanwhile, selecting more than 4,000 hens from the material group, raising them in small-scale groups in a plurality of hen cages to 18 weeks of age, eliminating weak hen individuals in the raising, and maintaining the number of the hens in the hen cages after the weak hen individuals are eliminated;

step B, forming breeding groups, including: at the end of the 18 weeks of age in the F1 generation group, selecting cock groups from cock cages each cock group includes at least 10 cocks meeting a breed criteria as breeding candidate groups, selecting hen groups from hen cages each hen group includes at least 30 hens meeting the breed criteria as breeding candidate groups, otherwise, eliminating a whole cage; according to a number of the selected cock cages, providing breeding cages with the same number as that of the cock cages to breed small-scale groups of cocks and hens to form the breeding groups, wherein the cocks and hens in each of the breeding cages come from a same cock cage and hen cage, respectively;

step C, screening the breeding groups, including: when the F1 generation group is over 25 weeks of age, performing a semen quality determination on the cocks of the breeding candidate groups in the breeding groups, eliminating cock individuals with unqualified semen quality, and if more than 3 cock individuals are eliminated in a single breeding cage, then simultaneously eliminating the cocks and hens in the breeding cage; otherwise keeping the cocks and hens in the breeding cage as a breeding group for natural mating; when the F1 generation group is at the end of 32 weeks of age, performing determinations of a fertilization rate and a hatching rate on the breeding groups in each of the breeding cages, counting an egg production from a start of production to 32 weeks of age, the fertilization rate at 32 weeks of age, and the hatching rate at 32 weeks of age in each of the breeding cages, and formulating a comprehensive selection index, selecting the breeding groups having the comprehensive selection index of a top 80% for breeding offspring;

step D, forming a F2 generation group, including: collecting a sufficient number of breeding eggs for hatching, and hatching the breeding eggs of each breeding cage to breed F2 generations independently; wherein when the F1 generation group is at the end of 38 weeks of age, the F2 generation group emerges, and selecting healthy chicks meeting the breed criteria to form the F2 generation group; and step E, grouping cocks and hens in the F2 generation group and raising the cocks and hens in the brooding/breeding cages to the end of 10 weeks of age, and repeating steps A to C to continue breeding to a F (N) generation group.

Preferably, the further technical solution is as follows: the variation coefficients of weight and appearance uniformity of the cocks and the hens selected from the material group in the step A are both less than or equal to 10%, the number of cock cages is at least 100 with 20 cocks per cage, and the number of hen cages is at least 100 with 40 hens per cage.

A further technical solution is as follows: the number of breeding cages in the step B is at least 80, and 6 cocks and 30 hens are selected for raising in small-scale group in each of the breeding cages.

A further technical solution is as follows: in the step C, the semen quality of the cocks in the breeding group is determined and the number of the breeding cages that are finally selected as the breeding groups is at least 60.

A further technical solution is as follows: in the step C, the breeding cages selected as the breeding groups are numbered, and since the hens start to produce, and a number of the produced eggs and a number of deaths and eliminations in the group of each of the breeding cages are recorded; in the step E, the brooding cages of a F (N+1) generation group are numbered correspondingly according to the numbers of the breeding cages of the F (N) generation group.

A further technical solution is as follows: after the fertilization rate and the hatching rate of the breeding groups in each of the breeding cages are determined in the step D, the number of the breeding cages selected as the breeding groups is at least 40.

A further technical solution is as follows: the step E further includes that at the end of 18 weeks of age in a F (N+1) generation group, cocks and hens in a same breeding cage cannot come from a same breeding cage in the F (N) generation; at the end of 32 weeks of age, when selecting the F (N) generation breeding group for breeding the F (N+1) generation, it is necessary to comprehensively consider the egg production at 32 weeks of age, the fertilization rate at 32 weeks of age, the hatching rate at 32 weeks of age, and the egg production at 66 weeks of age in the F (N−1) generation.

Compared with the prior art, one of the advantages of the present invention is as follows: this method includes raising in small-scale groups and natural mating for systematic selection and breeding, which effectively reduces the generation interval and has the features of easy operation and fast genetic progress, not only ensuring animal welfare, but also effectively improving production performance. Additionally, in the breeding method for improving the reproductive performance of the chicken specialized dam line provided by the present invention, the chicken specialized dam line is characterized by genetically superior breeding traits, including high reproductive performance, low pecking rate, and high survival rate. The group is further characterized by highly desirable intangible selected traits: less prone to aggressive behavior and fighting, calm and quiet and high production performance. Therefore, the present invention has significant scientific value and economic value for improving the breeding technology of chickens and reducing the production cost of breeding chickens in China.

DETAILED DESCRIPTION OF THE EMBODIMENTS

The present invention is further described below in combination with specific embodiments.

The embodiment of the present invention is a breeding method for improving reproductive performance of a chicken specialized dam line. This embodiment includes and preferably performs the following steps to breed chickens of breeding groups to ensure that the above technical objectives are achieved. The specific steps are as follows.

Step S1. 8000 chicks of Daheng S05 line are introduced as the specialized dam line material to form a F1 generation group. Cocks and hens are grouped and raised in brooding/breeding cages to the end of 10 weeks of age.

Step S2. At the end of 10 weeks of age in the F1 generation group, more than 2,000 cocks with variation coefficients of weight and appearance uniformity equal to or less than 10% are selected to raise in small-scale groups in cock cages with 20 cocks per cage, and more than 100 cock cages are prepared. The cocks are raised to 18 weeks of age, the weak cock individuals in the raising are eliminated, the number of the cocks in the cock cages is maintained after the weak cock individuals are eliminated, and other cocks are not placed in the cock cages after the weak cock individuals are eliminated in the raising. More than 4,000 hens with variation coefficients of weight and appearance uniformity equal to or less than 10% are selected to raise in small-scale groups in hen cages with 40 hens per cage, and more than 100 hen cages are prepared. The hens are raised to 18 weeks of age, the weak hen individuals in the raising are eliminated, the number of the hens in the cock cages after the weak cock individuals are eliminated is maintained, and other hens cannot be put into the hen cages after the weak hen individuals are eliminated in the raising.

In this step, preferably, the cock cages used are large square cages customized according to breed features, and each of the cock cages can raise 20 adult cocks. The hen cages are large square cages customized according to breed features, and each of the hen cages can raise 40 adult hens. The cock cages and hen cages each provide an active area of equal to or more than 700 $cm^2$ for each adult chicken.

Step S3. At the end of 18 weeks of age in the F1 generation group, the cock groups in the cock cages having at least 10 cocks meeting a breed criteria are selected as breeding candidate groups. Cock groups in the cock cages having 9 cocks or less are entirely eliminated. Hen groups in the hen cages having at least 30 hens meeting the breed criteria are selected as breeding candidate groups. Hen groups in the hen cages having 29 hens or less are entirely eliminated.

In this step, preferably, according to a number of the selected cock cages, breeding cages with the same number as that of the cock cages are provided. At least 80 breeding cages are required. 6 cocks and 30 hens are selected to raise in small-scale groups in each of the breeding cages. Cocks in each of the breeding cages come from the same respective cock cage, and hens in each of the breeding cages come from the same respective hen cage. Moreover, the breeding cages are large square cages customized according to breed features. The cocks and hens naturally mate in the cages. Each of the breeding cages can raise 36 adult chickens. The breeding cage provides an active area of equal to or more than 700 $cm^2$ for each adult chicken.

Step S4. When the F1 generation group is about 25 weeks of age, a semen quality determination on each of the cocks of the respective breeding candidate groups is performed. Cock individuals with unqualified semen quality are eliminated. If more than 3 cocks are eliminated in a single breeding cage, then the cocks and hens in that breeding cage are simultaneously eliminated. If more than 3 cocks have qualified semen quality in a single breeding cage, the cocks and hens in that breeding cage are kept as a breeding group for natural mating and a corresponding performance determination is performed. The number of the selected breeding cages is required to be equal to or more than 60.

It should be noted that in this step, the breeding cages selected for breeding are numbered. Since the hens will have begun to produce, the number of eggs produced and the number of corresponding deaths and eliminations of each breeding cage are recorded daily.

Step S5. When the F1 generation group is at the end of 32 weeks of age, a corresponding fertilization rate and a corresponding hatching rate for each of the breeding cages are performed. An egg production from a start of production to 32 weeks of age, the fertilization rate at 32 weeks of age, and the hatching rate at 32 weeks of age in each of the breeding cages are counted. A comprehensive selection index is formulated according to an actual situation. The breeding groups having a comprehensive selection index in the top 80% are selected for breeding offspring. More than 40 breeding cages are required to be maintained for breeding. In this step, the corresponding data of the above fertilization rates and hatching rates is obtained through the observation and calculation methods commonly used in poultry breeding, so it is not described in detail in this embodiment.

Step S6: At the end of 35 weeks of age in the F1 generation group, a sufficient number of breeding eggs is collected for hatching. The breeding eggs of each breeding cage are hatched to breed F2 generation independently. The egg production data of the group of each corresponding breeding cage is recorded to the end of 66 weeks of age.

Step S7. When reaching the end of 38 weeks of age, the F2 generation group emerges. The chick group in the F2 generation is numbered in corresponding fashion to the numbers in the breeding cage in the F1 generation group. The healthy chicks that meet the breed criteria are selected to prepare for raising, breeding and selection of the F2 generation group.

Step S8. The cocks and hens in the F2 generation group are grouped and raised in the brooding/breeding cages to the end of 10 weeks of age. The breed selection and mate selection of the F1 generation group are repeated; however, differences are as follows: (1) At the end of 18 weeks of age, the cocks and hens in a same breeding cage in the F2 generation group cannot come from a same breeding cage in the F1 generation group, thereby avoiding inbreeding. (2) At the end of 32 weeks of age, the determination and analysis of the F2 generation group are performed. The following criteria are considered in selecting the F2 generation group for breeding a F3 generation group (i) egg production at 32 weeks of age, (ii) the fertilization rate at 32 weeks of age, (iii) the hatching rate at 32 weeks of age, and (iv) the egg production at 66 weeks of age in the F1 generation group.

Step 9. The processes and methods described for the breed selection and mate selection of the F2 generation group are repeated for subsequent generations. The F3 generation group or the Fn generation group can be continuously selected according to this method.

Based on the above embodiment of the present invention, the breeding of 5 continuous generations is performed through the above steps. The generation interval is shortened from 52 weeks in traditional pedigree breeding to 38 weeks, which is a reduction of 26.92% Such time savings indirectly improves the breeding progress of each generation. The egg production of the 66-week-old Daheng S05 line increases from 168 in the F1 generation to 183, an 8.93% increase, with an average genetic progress per generation of three eggs. This is in comparison with one egg for the average per-generation genetic progress of breeding performance of the chicken specialized dam line both at home and abroad. The breeding efficiency is increased by two times. The number of healthy chicks per breeding chicken increases from 110 in the F1 generation to 126, an increase of 14.5%. The mortality of breeding chickens at 18-66 weeks of age decreases from 21.3% to 8.58%, with an average reduction of 2.54% per generation. The direct gain effect of increasing the group survival rate and improving the reproductive performance reduces the breeding production cost by more than 10%, achieving significant economic benefits. The new method provides substantial incentive for the popularization and application of the breeding method for the reproductive performance of the dam line in the present invention.

The terms "breeding" and "brooding" as used interchangeably throughout the specification to mean breeding.

In addition to the above, it should be noted that the terms "one embodiment", "another embodiment" and "embodiment" described in this specification refer to that specific characteristics, structures, or features described in combination with this embodiment are included in at least one embodiment described generally in the present disclosure. The presentation of the same expression in multiple places in the specification does not necessarily refer to the same embodiment. Further, when describing a specific feature, structure or characteristic in combination with any embodiment, the claimed implementation of such feature, structure or characteristic in combination with other embodiments is still within the scope of the present invention.

Although the present invention is described herein with reference to a number of illustrative embodiments, it should be understood that those skilled in the art can devise many other modifications and implementations, and such modifications and implementations shall fall within the scope and spirit of the principles disclosed in the present disclosure. More specifically, within the scope of the present specification and claims, various variations and improvements in the component parts of the subject combination arrangements and/or arrangements can be made. In addition to variations and modifications in the component parts and/or the arrangements, other uses are also may be apparent to those skilled in the art.

What is claimed is:

1. A breeding method for improving reproductive performance of a chicken specialized dam line, comprising the following steps:

step A, forming a first generation group, comprising: introducing breeding chickens of a specialized dam line as a breeding material, grouping cocks and hens in the breeding chickens to obtain grouped cocks and grouped hens, and raising the grouped cocks and the grouped hens in brooding/breeding cages to 10 weeks of age to form a material group; then, selecting more than 2,000 cocks from the material group, raising the more than 2,000 cocks in small-scale groups in a plurality of cock cages to 18 weeks of age, eliminating weak cock individuals in the raising, and maintaining remaining cocks in the plurality of cock cages after the weak cock individuals are eliminated; meanwhile, selecting more than 4,000 hens from the material group, raising the more than 4,000 hens in small-scale groups in a plurality of hen cages to 18 weeks of age, eliminating weak hen individuals in the raising, and maintaining remaining hens in the plurality of hen cages after the weak hen individuals are eliminated;

step B, forming breeding groups, comprising: at an end of 18 weeks of age in the first generation group, selecting cock groups in a first plurality of cock cages as breeding candidate groups to obtain a number of selected cock cages, wherein each of the first plurality of cock cages comprises at least 10 cocks meeting a breed criteria; selecting hen groups in a first plurality of hen cages as breeding candidate groups to obtain a number of selected hen cages, wherein each of the first plurality of hen cages comprises at least 30 hens meeting the breed criteria; eliminating a second plurality of cock cages and a second plurality of hen cages, wherein each of the second plurality of cock cages comprises less than 10 cocks, and each of the second plurality of hen cages comprises less than 30 hens; according to the number of the selected cock cages, providing a number of breeding cages corresponding with the number of the selected cock cages to breed small-scale groups of cocks and hens to form the breeding groups, wherein the cocks and hens in each of the breeding cages come from a same cock cage in the selected cock cages and a same hen cage in the selected hen cages, respectively;

step C, screening the breeding groups, comprising: when the first generation group reaches 25 weeks of age, performing a semen quality determination on the cock groups of the breeding candidate groups in the breeding groups, eliminating cock individuals with unqualified semen quality, and if more than 3 cocks are eliminated in a single breeding cage, then simultaneously eliminating cocks and hens in the single breeding cage; otherwise keeping the cocks and the hens in the single breeding cage as a breeding group for natural mating; when the first generation group is at an end of 32 weeks of age, performing determinations of a fertilization rate and a hatching rate of the breeding groups in each of the breeding cages, counting an egg production from a start of production to 32 weeks of age, the fertilization rate at 32 weeks of age, and the hatching rate at 32 weeks of age in each of the breeding cages; formulating a comprehensive selection index and selecting the breeding groups having the comprehensive selection index of a top 80% as selected breeding groups for breeding offspring;

step D, forming a second generation group, comprising: collecting a predetermined number of breeding eggs of each breeding group of the selected breeding groups for hatching, and hatching the predetermined number of breeding eggs to breed the second generation group independently; when the first generation group is at an end of 38 weeks of age, the second generation group emerges, and selecting healthy chicks meeting the breed criteria to form the second generation group; and step E, grouping cocks and hens in the second generation group to obtain grouped cocks and grouped hens, and raising the grouped cocks and the grouped hens in the brooding/breeding cages to an end of 10 weeks of age, and repeating steps A to C to continue breeding to an $N^{th}$ generation group, wherein N is a natural number greater than 2.

2. The breeding method for improving the reproductive performance of the chicken specialized dam line according to claim 1, wherein in the step A, variation coefficients of weights and appearance uniformity of the more than 2,000 cocks and the more than 4,000 hens selected from the material group are both less than or equal to 10%, a number of the plurality of cock cages is at least 100, each of the plurality of cock cages comprises 20 cocks, and a number of the plurality of hen cages is at least 100, and each of the plurality of hen cages comprises 40 hens per cage.

3. The breeding method for improving the reproductive performance of the chicken specialized dam line according to claim 1, wherein in the step B, the number of the breeding cages is at least 80, and 6 cocks and 30 hens are selected for raising in a small-scale group in each of the breeding cages.

4. The breeding method for improving he reproductive performance of the chicken specialized dam line according to claim 1, wherein in the step C, a semen quality of each of the cock groups in the breeding groups is determined and a number of the breeding cages that are finally selected as the selected breeding groups is at least 60.

5. The breeding method for improving the reproductive performance of the chicken specialized dam line according to claim 4, wherein in the step C, the breeding cages selected as the selected breeding groups are numbered, and since the hens start to produce, a number of produced eggs and a number of deaths and eliminations in the group of each of the breeding cages are recorded; in the step E, the breeding cages of a $n^{th}$ generation group are numbered in corresponding fashion according to the numbers of the breeding cages of a $(n-1)^{th}$ generation group, wherein n is a natural number equal to or less than N.

6. The breeding method for improving the reproductive performance of the chicken specialized dam line according to claim 1, wherein in the step C, the breeding cages selected as the selected breeding groups are numbered, and since the hens start to produce, a number of produced eggs and a number of deaths and eliminations in the group of each of the breeding cages are recorded; in the step E, the breeding cages of a $n^{th}$ generation group are numbered in corresponding fashion according to the numbers of the breeding cages of a $(n-1)^{th}$ generation group, wherein n is a natural number equal to or less than N.

7. The breeding method for improving the reproductive performance of the chicken specialized dam line according to claim 6, wherein after the fertilization rate and the hatching rate of the breeding groups in each of the breeding cages are determined in the step C. the number of the breeding cages selected as the selected breeding groups is at least 40.

8. The breeding method for improving the reproductive performance of the chicken specialized dam line according to claim 1, wherein the step E further comprises that at the end of 18 weeks of age in an $n^{th}$ generation group, cocks and hens in a same breeding cage do not come from a same breeding cage in a $(n-1)^{th}$ generation; at the end of 32 weeks of age, when selecting the $(n-1)^{th}$ generation group for breeding the $n^{th}$ generation, evaluating the egg production at 32 weeks of age, the fertilization rate at 32 weeks of age, the hatching rate at 32 weeks of age, and the egg production at 66 weeks of age in a $(n-2)^{th}$ generation to make changes to the breeding method, wherein n is a natural number equal to or less than N.

* * * * *